US010566769B2

(12) United States Patent
Waddell (10) Patent No.: US 10,566,769 B2
(45) Date of Patent: *Feb. 18, 2020

(54) MODULAR ION GENERATOR DEVICE

(71) Applicant: Charles Houston Waddell, Roanoke, VA (US)

(72) Inventor: Charles Houston Waddell, Roanoke, VA (US)

(73) Assignee: Global Plasma Solutions, Inc., Savannah, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/003,327

(22) Filed: Jun. 8, 2018

(65) Prior Publication Data

US 2019/0139751 A1 May 9, 2019

Related U.S. Application Data

(63) Continuation of application No. 15/670,219, filed on Aug. 7, 2017, now Pat. No. 10,020,180.

(60) Provisional application No. 62/372,053, filed on Aug. 8, 2016.

(51) Int. Cl.
| *A61L 9/22* | (2006.01) |
| *H01T 23/00* | (2006.01) |
| *F24F 3/16* | (2006.01) |

(52) U.S. Cl.
CPC ............ *H01T 23/00* (2013.01); *A61L 9/22* (2013.01); *F24F 3/16* (2013.01); *F24F 2003/1682* (2013.01)

(58) Field of Classification Search
CPC .......... H01J 49/10; H01J 27/02; H01J 27/022; A61L 9/22; H01T 23/00; F24F 3/16; F24F 2003/1682
See application file for complete search history.

(56) References Cited

U.S. PATENT DOCUMENTS

| 6,744,617 | B2 * | 6/2004 | Fujii | H01T 23/00 |
| | | | | 361/230 |
| 9,849,208 | B2 | 12/2017 | Waddell | |
| 10,020,180 | B2 * | 7/2018 | Waddell | H01J 49/10 |
| 2006/0193100 | A1 * | 8/2006 | Izaki | H01T 23/00 |
| | | | | 361/220 |
| 2008/0160904 | A1 * | 7/2008 | Yi | F24F 13/06 |
| | | | | 454/309 |
| 2014/0078639 | A1 * | 3/2014 | Waddell | H01T 23/00 |
| | | | | 361/230 |
| 2014/0103793 | A1 * | 4/2014 | Nishida | H01T 19/04 |
| | | | | 313/231.71 |
| 2014/0233232 | A1 * | 8/2014 | Radermacher | F21V 23/003 |
| | | | | 362/249.01 |
| 2016/0167059 | A1 | 6/2016 | Waddell | |

(Continued)

*Primary Examiner* — Eliza W Osenbaugh-Stewart
(74) *Attorney, Agent, or Firm* — Clements Bernard Walker (57) ABSTRACT

The present invention provides methods and systems for a modular ion generator device that includes a bottom portion, two opposed side portions, a front end, a back end, and a top portion. A cavity is formed within the two opposed side portions, front end, back end, and top portion. At least one electrode is positioned within the cavity, and an engagement device is engaged to the front end and/or an engagement device engaged to the back end for allowing one or more modular ion generator devices to be selectively secured to one another.

19 Claims, 8 Drawing Sheets

(56) References Cited

U.S. PATENT DOCUMENTS

| | | |
|---|---|---|
| 2017/0232131 A1 | 8/2017 | Waddell |
| 2018/0071426 A1 | 3/2018 | Waddell |

* cited by examiner

MODULAR ION GENERATOR DEVICE

CROSS REFERENCE TO RELATED PATENT APPLICATION

This application is a continuation of U.S. patent application Ser. No. 15/670,219 filed Aug. 7, 2017 and entitled "MODULAR ION GENERATOR DEVICE" which claims the benefit of U.S. Provisional Patent Application No. 62/372,053, filed on Aug. 8, 2016, and entitled "MODULAR ION GENERATION DEVICE," the contents of which are incorporated in full by reference herein.

FIELD OF THE INVENTION

The present invention relates generally to an ion generator device, and more generally relates to a modular ion generator device that may be selectively secured to at least one other ionization bar and mounted to a number of locations on a cooling coil frame or elsewhere in the HVAC system.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering air for these and other applications. It is to the provision of improved systems and methods meeting these needs that the present invention is primarily directed.

Historically ionization bars have been custom manufactured for a specific application length, thus requiring a lead-time for manufacturing. The present invention solves the custom manufacturing lead-time issue by providing a standard size off-the-shelf modular bar at a fixed length that can be connected in any quantity for the length required for the given application.

BRIEF SUMMARY OF THE INVENTION

According to an embodiment of the present invention an ion generator device that includes a bottom portion, two opposed side portions, a front end, a back end, and a top portion. A cavity is formed within the two opposed side portions, front end, and back end. At least one electrode is positioned within the cavity, and an engagement device is engaged to the front end and a receptacle within the back end allowing one or more modular ion generator devices to be selectively secured to each other.

According to another embodiment of the present invention, the ion generator device wherein one or more modular ion generator devices are selectively secured to one another.

According to yet another embodiment of the present invention, the modular ion generator device includes a magnet positioned on the device for selectively securing the device to a cooling coil frame.

According to yet another embodiment of the present invention, the modular ion generator device includes at least one flange extending from the device for engaging a magnet thereto.

According to yet another embodiment of the present invention, the modular ion generator device includes a printed circuit board housed within the cavity and the at least one electrode that extends outwardly from the printed circuit board.

According to yet another embodiment of the present invention, the modular ion generator device includes an electrode constructed of carbon fiber brushes.

According to yet another embodiment of the present invention, the modular ion generator device includes a nipple extending upwardly from the top portion of the device.

According to yet another embodiment of the present invention, the modular ion generator device includes a bottom portion that extends to an outer edge, two opposed side portions that extend upward from the outer edge, a front end that extends upward from the outer edge, a back end that extends upward from the outer edge, and a top portion. A cavity is formed within the two opposed side portions, front end, and a back end. At least one bore is disposed on the top portion, and at least one electrode is positioned within the cavity and adjacent the bore. An engagement device is engaged to the front end and a receptacle within the back end for allowing one or more ion generator devices to be selectively secured to each other.

According to yet another embodiment of the present invention, the modular ion generator device includes a power head engaged to the engagement device of the modular ion generator device.

According to yet another embodiment of the present invention, the modular ion generator device includes a cylindrical outer portion, a front end, a back end, and an area for the emitters to be exposed to the airstream. A cavity is formed within the cylindrical outer wall, front end, back end, and ionizing portion. At least one electrode is positioned within the cavity, and an engagement device is engaged to the front end and a receptacle is engaged to the back end for allowing one or more ion generator devices to be secured together.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Referring now specifically to the drawings, an ion generator device is illustrated in FIGS. 1-10 and is shown generally at reference numeral 10. The device 10 includes a housing having a bottom portion 12 that extends to an outer edge and two opposed side portions 14, a front end 16, and a back end 18 extend upwardly from the outer edge of the bottom portion 12. The two opposed side portions 14, the front end 16, and the back end 18 may have an upper edge with a ridge for receiving a top portion 20. Alternatively, the top portion 20 may be engaged to the upper edge of the two opposed side portions 14, the front end 16, and the back end 18. A cavity 22 is formed within the bottom portion 12, two opposed side portions 14, front end 16, and back end 18. An ionizer 24, having at least one electrode 26, is housed within the cavity 22.

Figure 1:
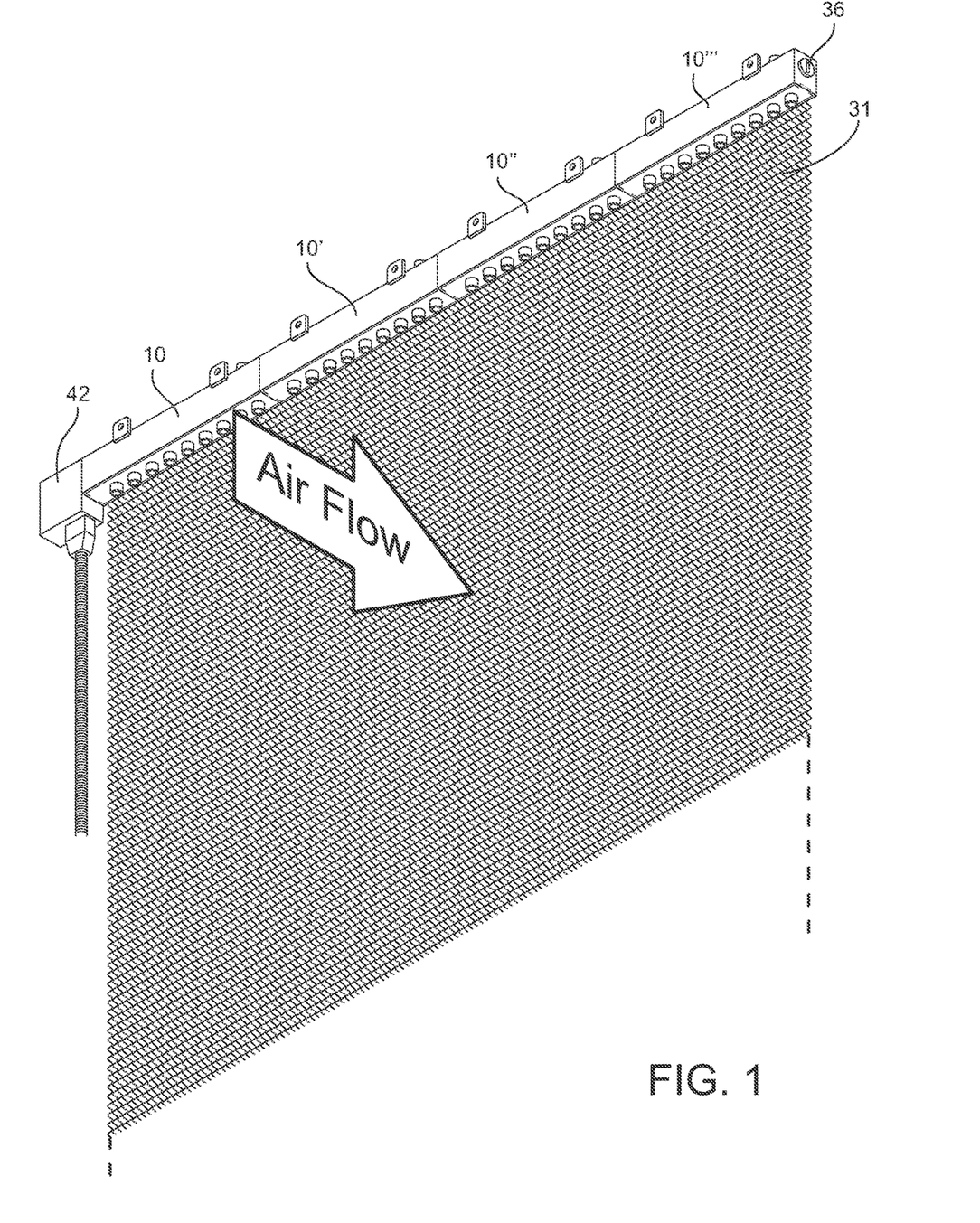
FIG. 1 is a perspective view of a plurality of ion generator devices engaged to each other above a coiling coil.
Figure 5:
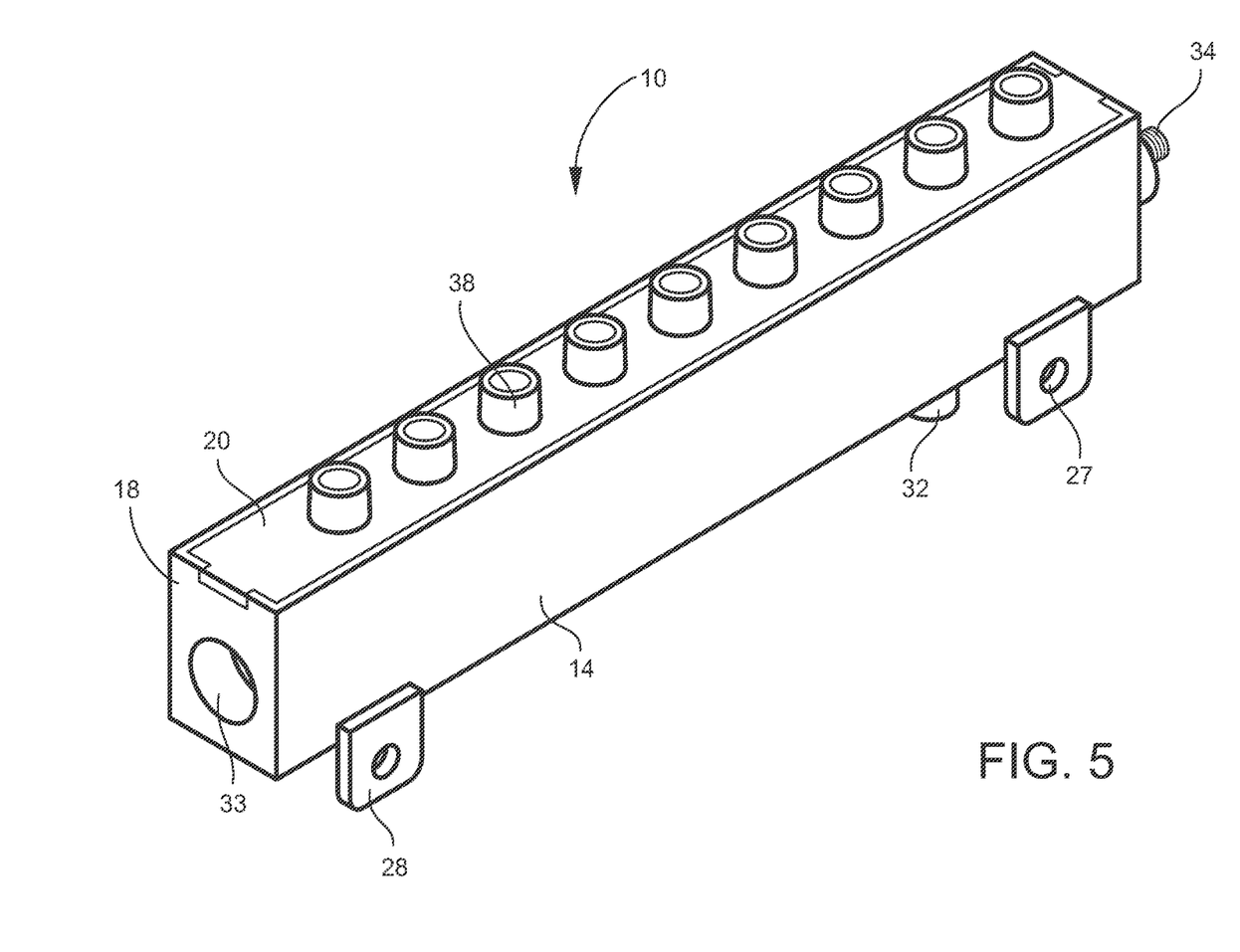
FIG. 5 is a perspective view of the ion generator device.
Figures 7A, 7B:
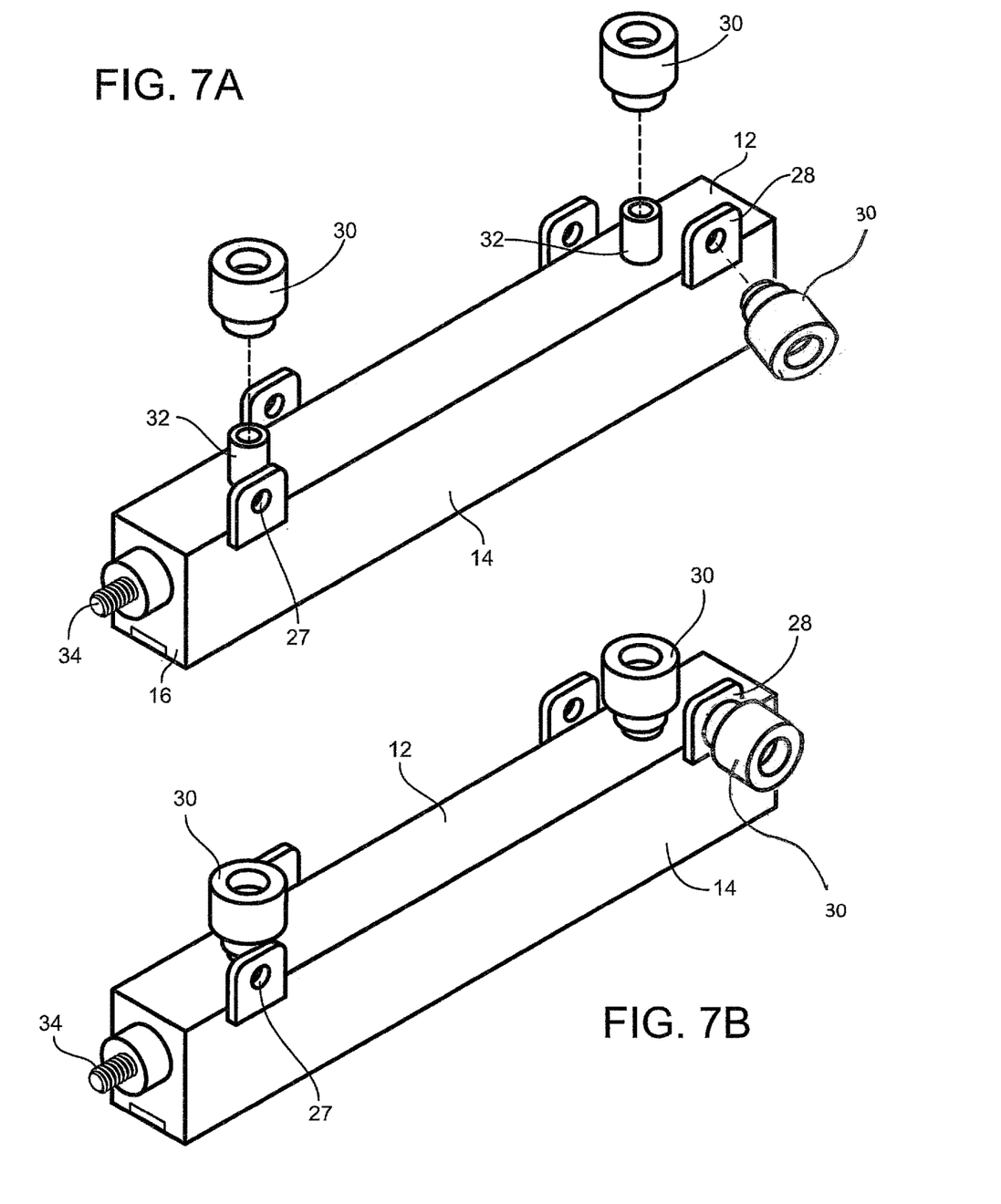
FIG. 7A is an exploded view of the ion generator device including magnets.
FIG. 7B is a perspective view of the ion generator device including magnets.

A pair of engagement flanges 28 are disposed on each of the two opposed side portions 14. The flanges extend away from the two opposed side portions 14 and contain a bore 27 within each flange 28. As shown in FIGS. 7A and 7B, a magnet 30 may be engaged to each flange 28. As illustrated, a circular magnet 30 may be engaged through the flange 28 with a portion of the magnet extending through the bore 27 and selectively securing the magnet 30 to the flange 28. In this arrangement, the device 10 may be face mounted to a coiling coil frame 31, as illustrated in FIG. 1, or elsewhere on the HVAC system. The magnet 30 may include a post on the back side of the magnet 30 that is received within the bore of each flange 28. The top portion 20 may also contain at least one post 32. The post 32, as shown in FIG. 5 may also receive a magnet 30. In this embodiment, the post 32 contains a bore for receiving a post on the back side of the magnet 30. In this arrangement, the device 10 may be mounting to the ceiling.

Figures 2, 3:
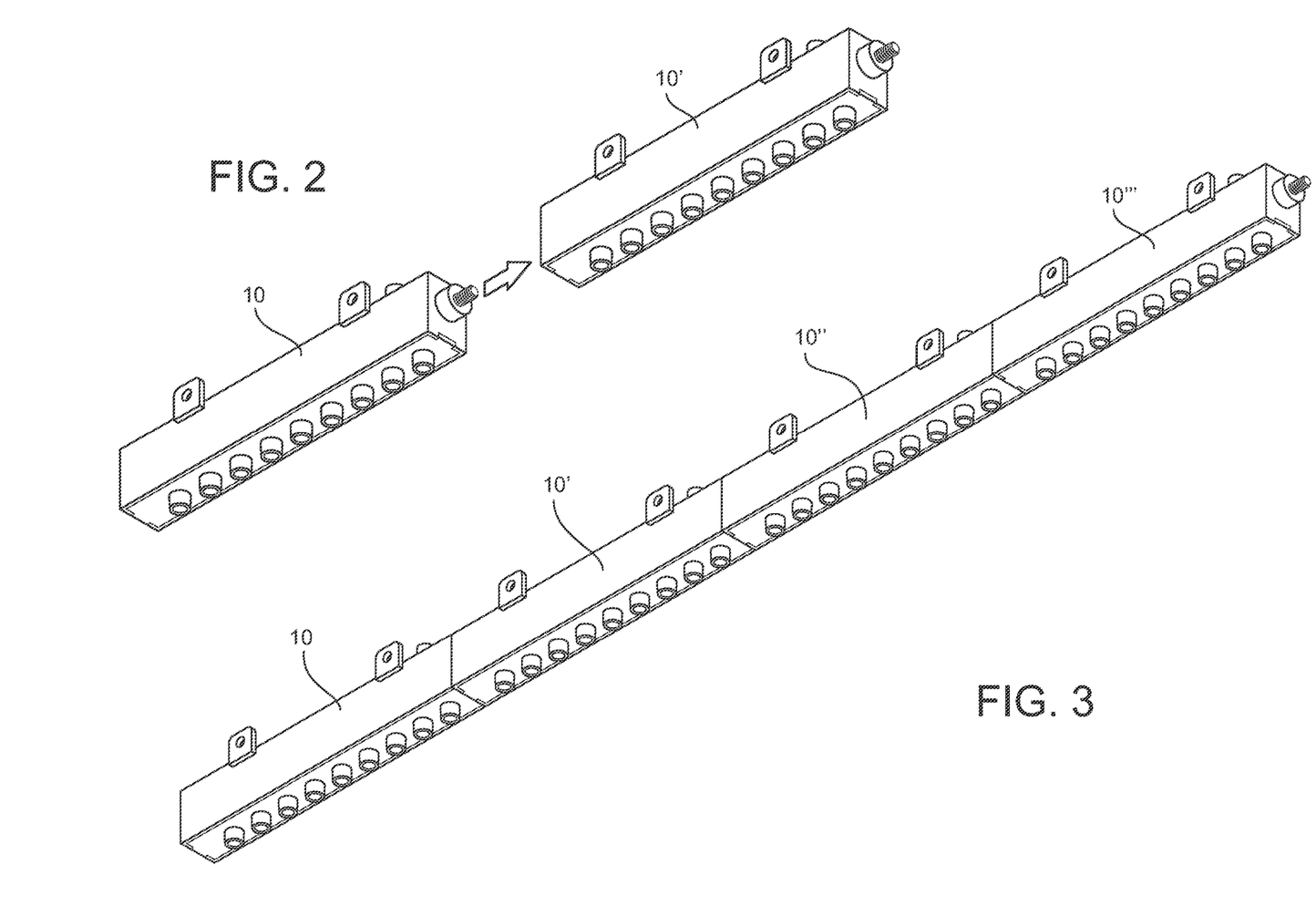
FIG. 2 is a top perspective view of the ion generator device engaged to a second ion generator device.
FIG. 3 is a perspective view of a plurality of ion generator devices selectively secured to each other.
Figure 4:
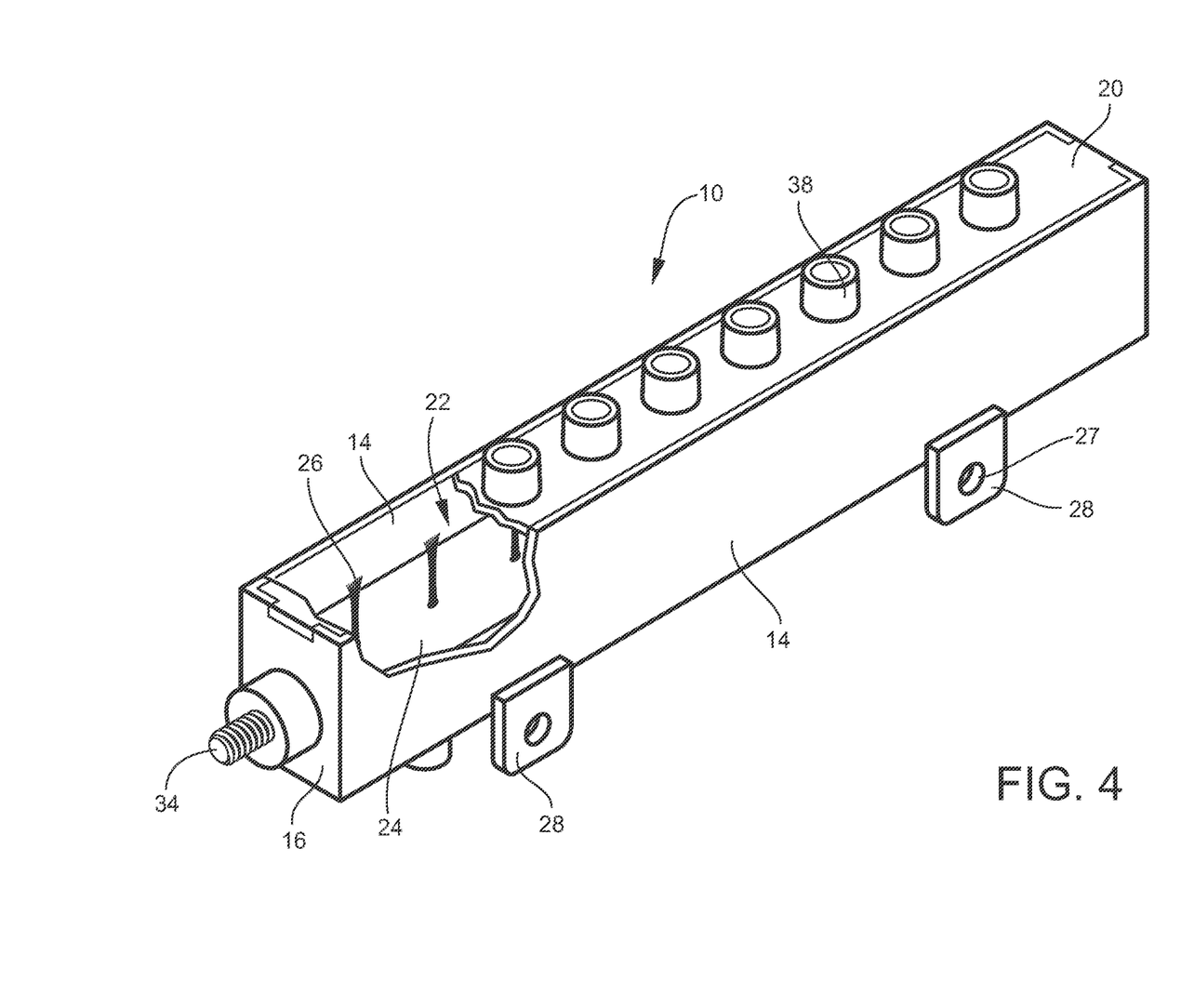
FIG. 4 is a partial cut-away view of an ion generator device.

The front end 16 contains an engagement device 34 that extends outward from the front end 16. As illustrated in FIGS. 4 and 5, the engagement device 34 is outwardly threaded. The back end 18 may contain a receptacle 33 that receives the engagement device 34 for selectively securing a first generator device with a second generator device. As illustrated in FIG. 5, the receptacle is correspondingly internally threaded for receiving the externally threaded engagement device 34 for selectively securing a first engagement device 34 to a second engagement device 34', as shown in FIG. 2. Additionally, the third engagement device 34" and fourth engagement device 34'" may be engaged to the first engagement device 34 and second engagement device 34', as shown in FIG. 3.

In an alternative embodiment, the engagement device 34 may be retained within the receptacle 33 by friction fit, or alternatively, the engagement device 34 may be magnetized, allowing the engagement device 34 to be selectively secured within the receptacle 33 or an end of the adjacent device 10. A cap 36 may be disposed within the receptacle 33 if no ionization device will be inserted into the receptacle 33.

The top portion 20 of the device 10 contains at least one nipple 38 that extends upwards from the top portion 20 and contains a hollow central portion that extends from the upper most surface of the nipple 38 to the cavity 22 of the device 10. The device 10 may contain two or more nipples 38 or a plurality of nipples 38. The electrode 26 is positioned adjacent the nipple 38. For example, the electrode 26 may be positioned inside the hollow central portion of the nipple 38 and below the opening contained within the upper most surface of the nipple 38. Alternatively, the electrode 26 may extend through the hollow central portion and above the opening within the upper most surface of the nipple 38. In another embodiment, the electrode 26 may be positioned entirely within the cavity 22, allowing the electrodes to proceed through the hollow central portion of the nipple and exiting the opening in the upper most surface of the nipple 38. The nipples 38 are centrally positioned and spaced-apart along the length of the top portion 20. The nipples 38 are disposed in a straight line along the length of the top portion 20.

Figure 6:
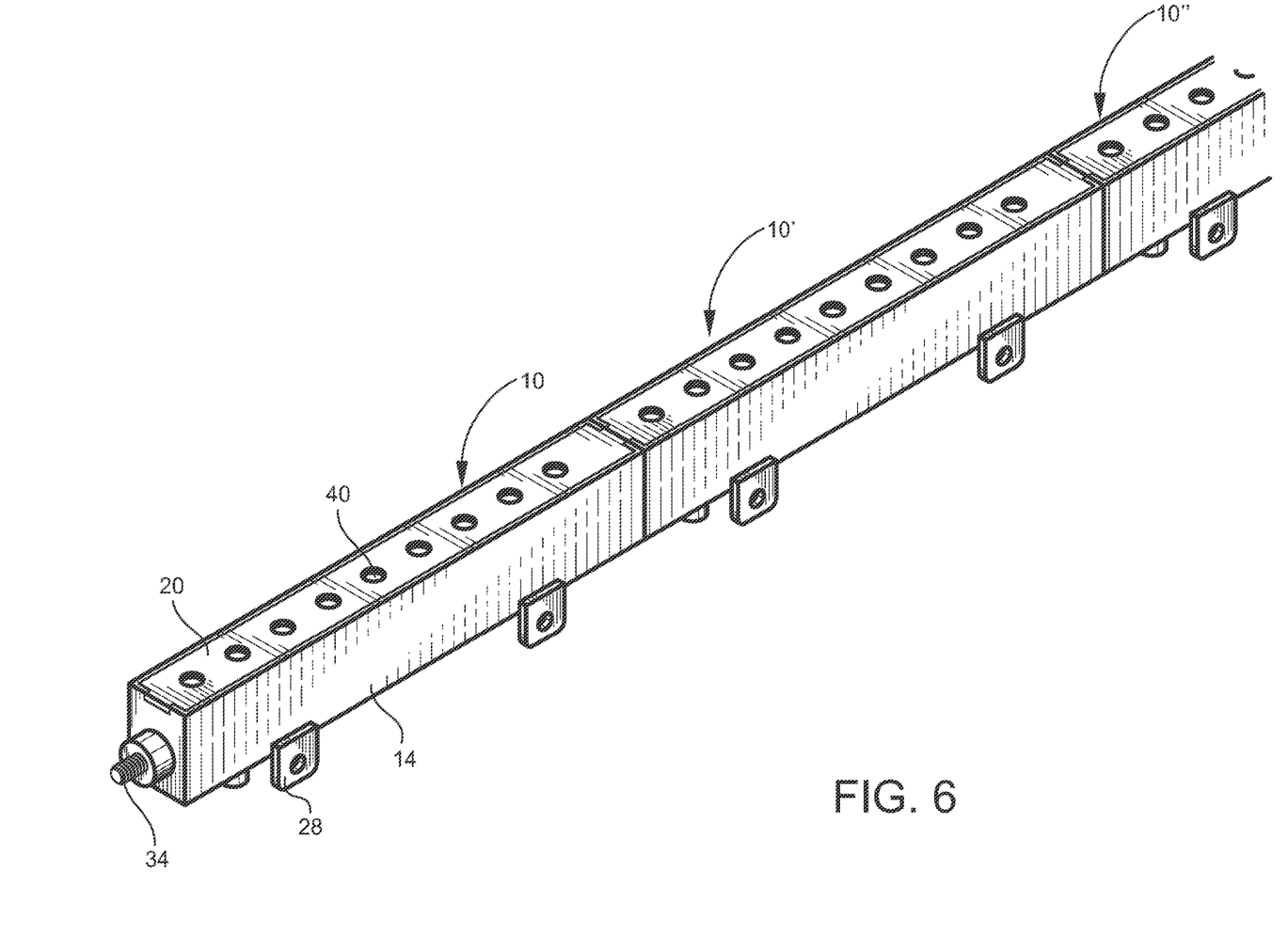
FIG. 6 is a perspective view of another embodiment of the ion generator device.

In another alternative embodiment as illustrated in FIG. 6, the device 10 may contain a plurality of openings 40 centrally positioned and spaced-apart along the length of the top portion 20. The openings 40 extend from the external surface of the top portion 20 to the internal surface of the top portion 20. The openings 40 are disposed in a straight line along the length of the top portion 20. The device 10 may contain one opening 40, two or more openings 40, or a plurality of openings 40. An electrode 26 is positioned adjacent the opening 40 for allowing ions to be emitted through the opening 40. Alternatively, the electrode 26 may extend through the opening 40 for emitting ions.

Figure 9:
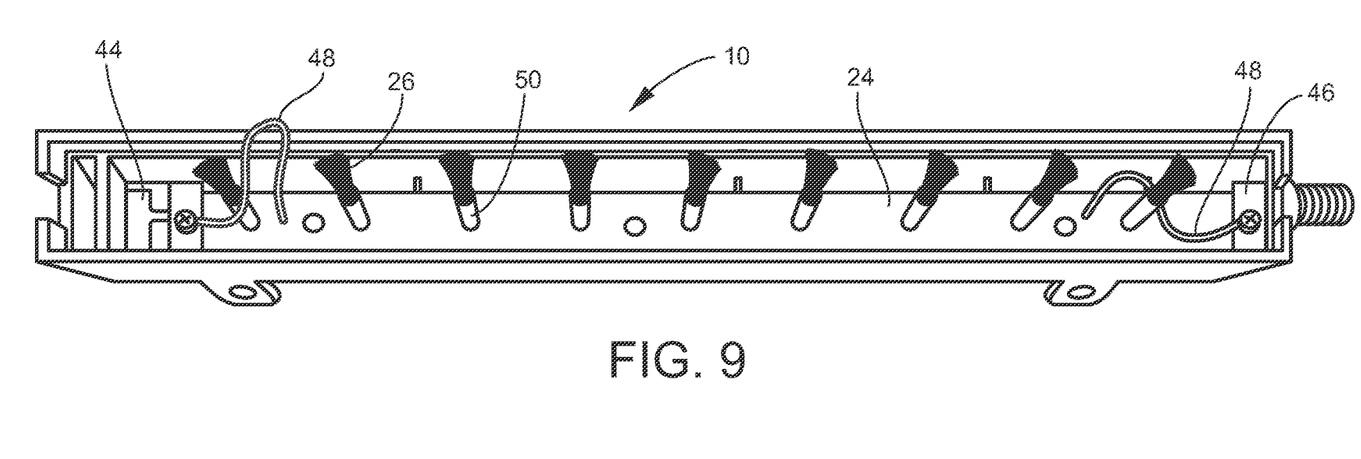
FIG. 9 is a top view of the ion generator device.
Figure 10:
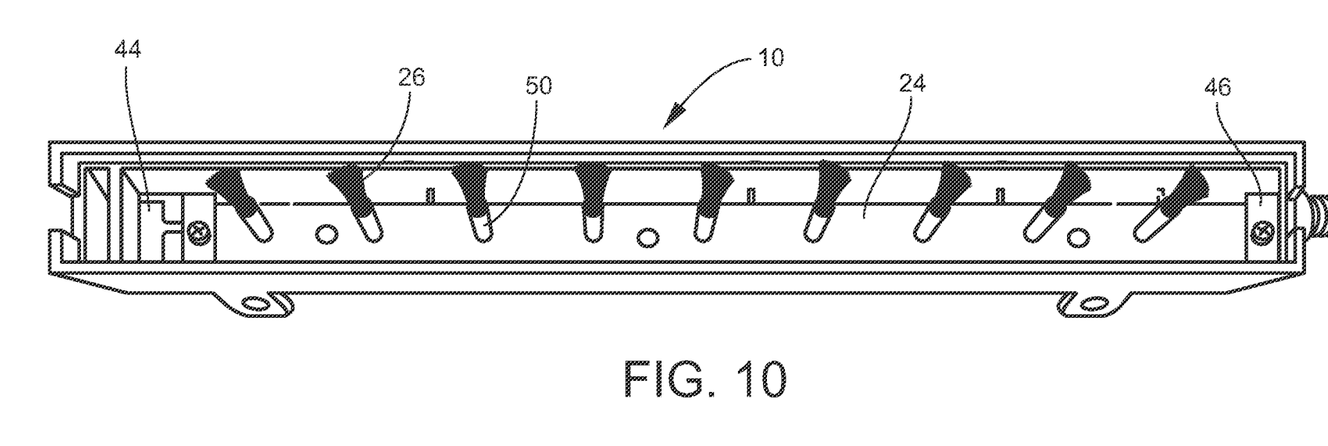
FIG. 10 is a top view of another embodiment of the ion generator device.

Each device 10 contains at least one electrode 26, two or more electrodes 26, or a plurality of electrodes 26. The electrodes are position on a printed circuit board 24 housed within the cavity 22 of the device 10. As illustrated in FIGS. 4, 9, and 10, the printed circuit board 24 generally extends along the length of the device 10 and between the front end 16 and back end 18. The printed circuit board 24 allows electricity to flow along the length of the device 10 and within the cavity of the device 10. The electrodes 26 extend upwardly from the printed circuit board 24. Electricity flows along the length of the printed circuit board 24, allowing a portion of the electricity to flow upwards along the length of the electrodes 26, allowing ions to flow from the end or ends of the electrode 26. An epoxy may be deposited within the cavity 22 and over the printed circuit board 24. Additionally, a sheath 50 may encompass a portion of the electrode 26. As shown in FIG. 10, the sheath 50 extends from the printed circuit board 24 and up a distance along the electrode 26, without enclosing the upper portion of the electrode 26.

The printed circuit board 24 may be engaged within the device 10 in two alternative arrangements. As illustrated in FIG. 9, a first electrical connector 44 and a second electrical connector 46 are positioned on either side of the cavity 22. The first electrical connector 44 may be positioned adjacent the internal side of the front end 16 and the second electrical connector 46 may be positioned adjacent the internal side of the back end 18. The first electrical connector 44 positioned adjacent the internal side of the front end 16 is coupled to the engagement device 34 for allowing electricity to flow from the engagement device 34 to the first electrical connector 44. The second electrical connector 46 is coupled to a conductive element within the receptacle 33 for allowing electricity to flow from the second electrical connector 46 to the receptacle and allowing the electricity to progress from the conductive element within the receptacle 33 to an engagement device 34 that may be selectively secured to the receptacle 33.

The first electrical connector 44 and second electrical connector 46 each contain an eye for receiving the first end of a wire 48. The second end of the wire 48 is engaged to an end of the printed circuit board 24 and allowing electricity to flow from the first connector 44 through the wire 48 to the first end of the printed circuit board 24. The electricity flow through the printed circuit board 24, allowing a portion of the electricity to flow through the electrodes 26 and producing ions, wherein the remainder of the electricity progresses down the printed circuit board 24 towards the second end. The remainder of the electricity flows to the second end of the printed circuit board 24 and through the wire 48 to the second electrical connector 46. A screw or other fastener may be used to engaged the first electrical connector 44, second electrical connector 46, and printed circuit board 24 to the device 10.

In another alternative embodiment, the first end of the printed circuit board 24 is engaged to the first electrical connector 44 and the second end of the printed circuit board 24 is engaged to the second electrical connector 46. The first electrical connector 44 and first end of the printed circuit board 24 each contain a hole, and the hole in the printed circuit board 24 is placed overtop the hole in the first electrical connector 44. A fastener, such as a screw, is inserted in the hole, allowing electricity to flow from the first connector 44 through the screw and into the printed circuit board 24. The second electrical connector 46 and second end of the printed circuit board 24 each contain a hole, and the hole in the printed circuit board 24 is placed overtop the hole in the second electrical connector 46. A fastener, such as a screw, is inserted in the hole, allowing electricity to flow from the printed circuit board 24 and into the second electrical connector 46.

In one embodiment, the electrodes 26 consist of a high voltage wire having a first end and a second end. The first end of the high voltage wire may contain a plurality of bristles or clusters that extend upwardly from the printed circuit board 24. The bristles are composed of any material that conducts electricity. The bristles or clusters may be composed of nylon, carbon fibers, or a thermoplastic polymer imbedded with conductive material that allows the polymer to conduct electricity. For example, the bristles may be composed of polypropylene or polyethylene and impregnated with carbon. Generally, the bristles of the electrode 26 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles. As illustrated in FIG. 4, the electrode consists of a plurality of carbon fibers having a first end and a second end. The first end is engaged to the printed circuit board 24 for receiving the flow of electricity flowing through the printed circuit board 24 and the second end extends upwardly from the printed circuit board 24 for emitting ions. Each fiber within the cluster can emit ions from its second end.

The device 10 may produce approximately equal amounts of positive and negative ions, regardless of airflow velocity or other conditions such as humidity or temperature. In example forms, the device 10 produces positive ions and negative ions in a concentration of at least about 40 million ions per cubic centimeter as measured 2 inches from the device electrodes. In alternate embodiments, the device generates negative ions only, or positive ions only, or generate negative ions and positive ions in unequal quantities.

In one embodiment, the top portion 20 of the device 10 may contain an LED bore that extends through the top portion 20 and into the cavity 22. An LED light may be positioned over the LED bore and engaged to an LED wire that extends from a circuit board to the LED light. When current is flowing through the high voltage wires current also flows through the LED wire and illuminates the LED light, indicating the device 10 is operating. The top portion 14 contains a first power supply bore and a second power supply bore for receiving the positive and negative power supply wires that serve as the power supply source.

The device 10 may be positioned and secured in place within the housing of the air handler unit such that the electrodes are aligned generally perpendicularly to the direction of the airflow across the device 10, to prevent recombination of the positively charged ions with the negatively charged ions.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

As shown in FIG. 1, a power head 42 provides, preferably AC current, to the device 10. Alternatively, the power head 42 could provide DC current. The power head 42 contains a female portion allowing the engagement device 34 of the device 10 to be inserted and mated to the power head. In one embodiment, the female portion of the power head 42 is internally threaded for the receiving the externally threaded engagement device 34 in a selectively secured arrangement. Selectively secured means the two devices, or in this instance power head 42 and device 10, can be separate from each other.

Figure 8:
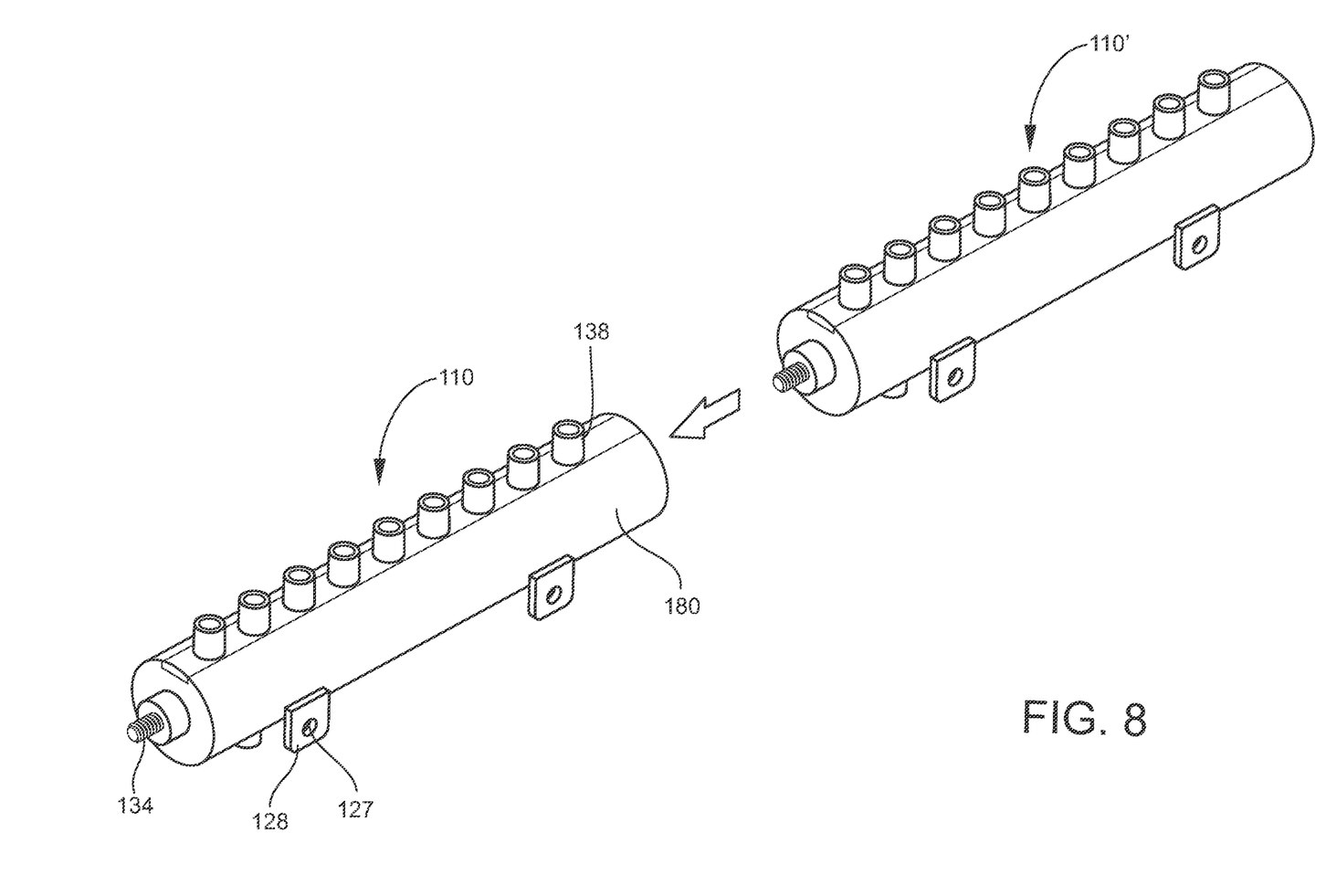
FIG. 8 is a perspective view of another embodiment of the ion generator device.

In another alternative embodiment, the device 110 may be composed of a generally cylindrical housing 180 having a front end 116 and a back end 118. The housing 180 may have an inner cavity having a printed circuit board 124 disposed therein and at least one opening 140 within the housing for allowing an electrode of the ionizer to emit ions outside the housing 180. The housing may also contain nipples 138, as described above, allowing ions to exit from the device 10. The front end 116 contains an engagement device 134 that extends outward from the front end 116. The back end 118 may contain a receptacle 133 that receives the engagement device 134 for selectively securing a first generator device 110 with a second generator device 110'. The engagement device 134 may be retained within the receptacle 133 by friction fit, or alternatively, the engagement device 134 may be magnetized, allowing the engagement device 134 to be selectively secured within the receptacle 133.

At least one engagement flange 128 may be disposed on the exterior surface of the generally circular housing 180. The flanges 128 extend upwards and contain a bore 127 within each flange. A magnet 130 may be engaged to each flange 128. In this arrangement, the device 110 may be face mounted to a coiling coil frame or elsewhere on the HVAC system. The magnet 130 may include a post 132 on the back side of the magnet 130 that is received within the bore 127 of each flange 128. The external surface of the generally circular housing 180 may also contain at least one post 132. The post 132 may also receive a magnet 130. In this embodiment, the post 132 contains a bore for receiving the back side of the magnet. In this arrangement, the device 10 may be mounted to the ceiling.

The electrodes within the ionizer may be removable or replaceable. The emitter points may be constructed of conductive resins, gold, titanium, or any other corrosion resistant conductive material.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generator device, comprising:
   a bottom portion, two opposed side portions, a front end, a back end, and a top portion;
   a cavity formed within the two opposed side portions, front end, back end, and top portion;
   a plurality of openings positioned along the top portion;
   at least one electrode positioned within the cavity and adjacent the openings;
   an engagement device engaged to the front end and a receptacle within the back end for receiving a second engagement device engaged to a second modular ion generator device for allowing one or more modular ion generator devices to be selectively secured to each other; and
   a printed circuit board housed within the cavity and the at least one electrode extends outwardly from the printed circuit board.

2. The modular ion generator device of claim 1, wherein one or more modular ion generator devices are selectively engaged to one another.

3. The modular ion generator device of claim 1, further comprising a magnet positioned on the device for selectively securing the device to a metal surface.

4. The modular ion generator device of claim 1, further comprising at least one flange extending from the device.

5. The modular ion generator device of claim 1, where the at least one electrode is constructed of carbon fiber brushes.

6. An ion generator device, comprising:
   a bottom portion that extends to an outer edge, two opposed side portions that extend upward from the outer edge, a front end that extends upward from the outer edge, a back end that extends upward from the outer edge, and a top portion;
   a cavity formed within the two opposed side portions, front end, and back end;
   a plurality of openings disposed on the top portion;
   a plurality of electrodes positioned within the cavity and each opening has an electrode disposed adjacent the opening;
   an engagement device engaged to the front end that is externally threaded and a receptacle within the back end that is internally threaded for allowing one or more ion generator devices to be selectively secured to each other; and
   a printed circuit board housed within the cavity and the at least one electrode extends outwardly from the printed circuit board.

7. The modular ion generator device of claim 6, further comprising a power head engaged to the modular ion generator device.

8. The modular ion generator device of claim 6, further comprising a magnet positioned on the device for selectively securing the device to a metal surface.

9. The modular ion generator device of claim 6, further comprising at least one flange extending from the device for engaging a magnet thereto.

10. The modular ion generator device of claim 6, further comprising at least one nipple extending from the top portion.

11. The modular ion generator device of claim 6, where the at least one electrode may be constructed of carbon fiber brushes.

12. The ion generator device of claim 6, wherein the engagement device is an externally threaded screw.

13. The ion generator device of claim 6, wherein the receptacle is an internally threaded bore.

14. An ion generator device, comprising:
   a cylindrical outer portion, a front end, and a back end;
   a cavity formed within the cylindrical outer wall, front end, and back end;
   a printed circuit board disposed within the cavity;
   a plurality of openings disposed on the cylindrical outer portion;
   a plurality of electrodes positioned within the cavity and engaged to the circuit board; and
   an engagement device engaged to the front end and/or an engagement device engaged to the back end for allowing one or more modular ion generator devices to be secured together.

15. The ion generator device of claim 14, wherein one or more modular ion generator devices are selectively engaged to one another.

16. The ion generator device of claim 14, further comprising a magnet positioned on the device for selectively securing the device to a metal surface.

17. The ion generator device of claim 14, further comprising at least one flange extending from the device for engaging a magnet thereto.

18. The ion generator device of claim 14, where the electrodes may be removable.

19. The ion generator device of claim 14, where the electrodes may be constructed of carbon fiber brushes.

* * * * *

UNITED STATES PATENT AND TRADEMARK OFFICE
CERTIFICATE OF CORRECTION

Page 1 of 1

PATENT NO. : 10,566,769 B2
APPLICATION NO. : 16/003327
DATED : February 18, 2020
INVENTOR(S) : Charles Houston Waddell

It is certified that error appears in the above-identified patent and that said Letters Patent is hereby corrected as shown below:

On the Title Page

Item (63) Related U.S. Application Data:
Change "Continuation of application No. 15/670,219 filed on Aug. 7, 2017, now Pat. 10,020,180" to This application is a continuation of application No. 15/670,219 filed on Aug. 7, 2017, now Pat. 10,020,180 which claims benefit of Provisional application No. 62/372,053, filed on Aug. 8, 2016.

Item (60) Related U.S. Application Data:
Delete "Provisional application No. 62/372,053, filed on Aug. 8, 2016"

Signed and Sealed this
Seventh Day of April, 2020

Andrei Iancu
*Director of the United States Patent and Trademark Office*